(12) United States Patent
Reed (10) Patent No.: US 7,086,285 B2
(45) Date of Patent: Aug. 8, 2006

(54) NONDESTRUCTIVE INSPECTION METHOD AND SYSTEM THEREFOR

(75) Inventor: Francis Alexander Reed, Princetown, NY (US)

(73) Assignee: General Electric Company, Schenectady, NY (US)

( * ) Notice: Subject to any disclaimer, the term of this patent is extended or adjusted under 35 U.S.C. 154(b) by 23 days.

(21) Appl. No.: 11/026,274

(22) Filed: Dec. 31, 2004

(65) Prior Publication Data

US 2006/0144149 A1 Jul. 6, 2006

(51) Int. Cl.
*G01N 9/00* (2006.01)

(52) U.S. Cl. .............................. 73/629; 73/597; 73/599; 73/602

(58) Field of Classification Search .................. 73/629, 73/597, 599, 602, 38, 588, 598, 618, 620, 73/633, 644
See application file for complete search history.

(56) References Cited

U.S. PATENT DOCUMENTS

| | | | |
|---|---|---|---|
| 5,031,457 A | * | 7/1991 | Kline ........................... 73/597 |
| 5,127,268 A | * | 7/1992 | Kline ........................... 73/597 |
| 5,181,421 A | * | 1/1993 | Kline ........................... 73/597 |
| 6,920,790 B1 | * | 7/2005 | Huang et al. .................. 73/597 |

* cited by examiner

*Primary Examiner*—Hezron Williams
*Assistant Examiner*—Jacques Saint Surin
(74) *Attorney, Agent, or Firm*—Ernest Cusick; Gary M. Hartman; Domenica N.S. Hartman (57) ABSTRACT

A method and system for determining the fiber volume fraction of a composite structure. The system includes a unit for ultrasonically determining the porosity volume fraction in the article, and a unit for calculating the volume fraction of the fibrous reinforcement material in the article based on the porosity volume fraction in the article and the mass densities of the article and the fiber and matrix materials within the article. The method entails determining the mass density of the article, obtaining the mass densities of the fiber material and the matrix material, ultrasonically determining the porosity volume fraction in the article, and then calculating the volume fraction of the fibrous reinforcement material in the article based on the porosity volume fraction in the article, the mass density of the article, the mass density of the matrix material, and the mass density of the fiber material.

20 Claims, 3 Drawing Sheets

NONDESTRUCTIVE INSPECTION METHOD AND SYSTEM THEREFOR

BACKGROUND OF THE INVENTION

The present invention generally relates to nondestructive inspection methods and systems. More particularly, this invention relates to a method and system for nondestructively determining the fiber volume of a composite material, such as fiber-reinforced polymer matrix structure.

Composite materials generally comprise a fiber reinforcement material embedded in a matrix material, such as a polymer or ceramic material. The reinforcement material serves as the load-bearing constituent of the composite material, while the matrix protects the reinforcement material, maintains the orientation of its fibers, and serves to dissipate loads to the reinforcement material. In view of the important role that fibers play in a composite material, fiber volume fraction is an important factor for determining the load carrying capability of a composite structure, an example of which is a low-density epoxy-graphite retaining ring taught in commonly-assigned U.S. Pat. No. 5,068,564 to Frank. Fiber volume fraction is, by definition, the amount of fibers making up the volume of a composite structure, and is an important measurement made to determine the quality of a composite structure and its ability to safely operate over its design life.

The most common method for determining fiber volume fraction in a polymer matrix composite material is acid digestion, which determines the weight fraction of fiber material in the material by etching away the polymer matrix material to leave only the fiber material. While accurate, this method is destructive since the material being evaluated is dissolved during the process. Therefore, while very useful for measuring the manufacturing process capability, acid digestion cannot be used to measure the fiber content of an actual part that will see service. Therefore, various nondestructive examination (NDE) techniques have been considered. For example, fiber contents of composite structures have been estimated on the basis of measuring elastic constants using ultrasonic wave propagation. These techniques measure the stiffness of the composite structure and, with a related calculation, determine the fiber content of the structure. However, a shortcoming of ultrasonic wave propagation techniques is that they require smooth and flat surfaces for precise ultrasonic measurements, a requirement that is not met by many composite structures. Also, these tests require precise ultrasonic measurements of time and position that are not possible with standard production-grade ultrasonic equipment and scanners.

Another limitation of ultrasonic techniques is that they are not suitable for inspecting composites that have a protective coating. An example of such a composite structure is the aforementioned composite epoxy-graphite retaining ring taught by Frank. A fiber volume fraction for the internal load-bearing section of the retaining ring is needed to verify that the ring will meet design requirements for full life. However, the addition of one or more protective layers affects the wave propagation on which ultrasonic measurements are based. As a result, ultrasonic techniques are generally impractical for use on many production composite structures.

In addition to fiber volume fraction, the presence of internal flaws in composite structures affects the life of these structures. The inspection of large metal components has led to the development of sophisticated x-ray, penetrant, and ultrasonic technologies for detecting surface and volumetric defects. However, composite product designs and manufacturing methods can create different types of defects than those created during the manufacture of metal structures. For example, composite structures can contain excess volumetric porosity that, if undetected, can lead to a drastically shortened component life. Therefore, nondestructive methods have also been developed for measuring the porosity content in composite components during their development for use as a design factor and during the manufacturing process to predict component life.

The most common method for measuring porosity in composite structures is the aforementioned acid digestion technique. When employed to determine porosity, the weight percent of matrix material and fiber material are measured separately by selectively etching only one of the materials. With knowledge of the mass density of the matrix and fiber materials, the percent porosity can be readily calculated. However, as discussed above in reference to measuring fiber volume fraction, acid digestion techniques are destructive and therefore their use is limited to a process control tool where either an entire component or a portion thereof can be sacrificed to measure the manufacturing process capability. It follows that acid digestion techniques cannot be employed to assess actual components that have or will see service.

As with efforts to measure fiber volume fraction, NDE techniques developed to nondestructively estimate porosity content have included sound attenuation. One approach is to calculate the acoustic scattering caused by porosity in a composite structure. For example, the use of attenuation slope measurements has been suggested for estimating porosity. Immersion-based attenuation measurement techniques have been proposed that correct for transducer diffraction and sound transmission losses. Attenuation slope measurements have been determined to be sensitive to the shape or aspect ratio of the pores, leading to the need for different coefficients to estimate the porosity content of composite structures produced by different composite construction techniques. Additional corrections have been identified for attenuation measurements made using focused immersion transducers, such as a correction for surface roughness losses and spatial filtering to correct for frequency-dependent focusing effects.

While the applicability of using ultrasonic attenuation techniques to estimate porosity has been demonstrated in laboratory settings, limitations exist for their practical use in manufacturing processes. For example, existing ultrasonic techniques require precision scanning of two transducers collecting data at multiple frequencies. Depending on the attenuation slope calculation method used, collecting the ultrasonic information needed to analyze porosity can require two or more scans of the composite structure. Because two transducers are required for these measurements with their positioning axes, and since most immersion tanks designed for metal inspection only have one transducer manipulator, the development of immersion tanks with two fully-controllable transducer manipulators would be required to implement existing ultrasonic attenuation techniques for use with composite components. Another shortcoming is the complexity of the calibration, measurements, and calculations required by these techniques.

In view of the above, it would be desirable if nondestructive methods existed for accurately measuring the fiber volume fraction and porosity in composite structures that can be readily implemented in a manufacturing setting.

BRIEF SUMMARY OF THE INVENTION

The present invention provides a method and system for determining the fiber volume fraction of a composite structure. This method of this invention is nondestructive and can be applied to structures that have external coatings or layers on its surface, and as such can readily be applied to production parts.

The system of this invention is adapted to ultrasonically inspect an article comprising a composite material that contains porosity and a fibrous reinforcement material in a matrix material. The system includes means for ultrasonically determining the volume fraction of the porosity in the article, and means for calculating the volume fraction of the fibrous reinforcement material in the article based at least on the volume fraction of the porosity in the article, the mass density of the article, the mass density of the matrix material, and the mass density of the fibrous reinforcement material.

The method of this invention is also adapted for ultrasonically inspecting an article comprising a composite material that contains porosity and a fibrous reinforcement material in a matrix material, and includes the steps of determining the mass density of the article, obtaining the mass density of the fibrous reinforcement material and the mass density of the matrix material, ultrasonically determining the volume fraction of the porosity in the article, and then calculating the volume fraction of the fibrous reinforcement material in the article based at least on the volume fraction of the porosity in the article, the mass density of the article, the mass density of the matrix material, and the mass density of the fibrous reinforcement material.

From the above, it can be appreciated that the method and system of this invention perform a nondestructive examination of an article, and therefore can be performed on production components that will later be placed in service. The invention enables the determination of the fiber volume fraction of a variety of composite structures, including those having external coatings or layers on surfaces thereof.

According to a preferred aspect of the invention, a nondestructive examination conducted in accordance with the invention can be performed with a single scan using a single ultrasonic transducer that generates and receives ultrasonic waves, instead of the multiple scans and transducers required by prior techniques. The use of a single transducer simplifies the calibration of the system and the inspection process, thereby greatly reducing the skill level required by the operator. The calibration and inspection steps of this invention are further simplified by operating the transducer to generate a single ultrasonic frequency during scanning. According to a preferred aspect of the invention, the volume fraction of the porosity is determined by measuring the attenuation of the ultrasonic waves as the ultrasonic waves travel through the article. By scanning the article, the volume fraction of the porosity can be determined for a plurality of locations on the article to yield a plurality of porosity data, which can then be displayed as a digital visual image.

Other objects and advantages of this invention will be better appreciated from the following detailed description.

DETAILED DESCRIPTION OF THE INVENTION

The present invention provides a nondestructive examination method and system for determining the fiber volume fraction of a composite article on the basis of the mass density ($\rho_a$) of the article, the mass density ($\rho_m$) of the matrix material of the article, the mass density ($\rho_f$) of the fiber material of the article, and the volume fraction ($v_p$) of porosity in the article. According to a preferred aspect of the invention, only two measurements of the actual composite article are required: the mass density of the composite article, and the porosity volume fraction. Other required information, such as the densities of the fiber and matrix materials of the composite article and any coating on the composite article, are characteristics of the materials that are usually available from various sources, such as the manufacturers of these materials. The volume of a coating can be calculated from the coating thickness, which can be nondestructively measured or accurately estimated based on the specified thickness applied during the deposition process.

According to a preferred aspect of the invention, the porosity for the composite article is measured using ultrasonic waves, to be discussed in detail below. The mass density of the composite article can be obtained by determining the mass of the article using commercially-available weight scales, and then calculating mass density by dividing the mass of the article by the volume of the article. The volume of a composite article having a uniform shape can be determined from linear measurements of the article. For composite articles having more complex shapes, density can be determined using the Archimedes Principle to determine the specific gravity of the article and then multiplying the value by the density of the immersion fluid (e.g., water).

The calculation of fiber volume fraction in accordance with this invention is based upon the principle that the total mass of the composite article is equal to the sum of the masses of its separate constituents or parts. For the case of a composite article that does not have a surface coating or layer, and comprises a polymer (e.g., resin) matrix material, a fiber reinforcement material, and porosity, the total mass of the article is equal to the combined mass of the fiber material, the matrix material, and the porosity ($m_a = m_m + m_f + m_p$). Since the mass of a substance is equal to the volume of the substance multiplied by the mass density of that substance, the above mass-based equation can be transformed into a density-based equation. The volume of each constituent of the composite article can be converted into a volume fraction measurement by dividing the volume of the constituent by the total volume of the composite article. These two operations convert the mass-based equation into the following equation in terms of density and volume fraction.

$$\rho_a = v_m \cdot \rho_m + v_f \cdot \rho_f + v_p \cdot \rho_p$$

where $\rho_a$ is the mass density of the article, $\rho_m$ is the mass density of the matrix material, $\rho_f$ is the mass density of the fiber material, $\rho_p$ is the mass density of the porosity, $v_m$ is the volume fraction of the matrix material, $v_f$ is the volume fraction of the fiber material, and $v_p$ is the volume fraction of the porosity.

By definition, the sum of the volume fractions must equal 1.0. Therefore, the volume fraction of the matrix is equal to 1 minus the volume fraction of the fiber minus the volume fraction of the porosity $(1-v_f-v_p)$. The density of the porosity is negligible in these calculations and can be assumed to be equal to 0.0. Substituting these two changes into the density equation yields the following equation.

$$\rho_a = (1-v_f-v_p)\cdot\rho_m + v_f\cdot\rho_f$$

Solving the above equation for the volume fraction of fibers in the composite article yields the following equation.

$$v_f = [\rho_a - (1-v_p)\cdot\rho_m]/(\rho_f-\rho_m)$$

By measuring the density of the composite article and the volume fraction of the porosity, and with knowledge of the densities of the fiber and matrix materials, the volume fraction of the fiber material within an uncoated composite article can easily be determined with the above equation.

If a coating or layer is present on a surface of the composite article, the mass, volume, and density of the entire article is modified. The fiber volume fraction calculation must also be modified to correct for the additional mass and volume associated with the coating or layer. Using a similar approach to that described above for an uncoated composite article, an additional term must be included for the mass of the coating. Since the density of coating materials are generally readily available, such as from suppliers of the materials, and the volume fraction of the coating can be directly measured or accurately estimated as previously explained, no additional measurements are required to calculate the fiber volume fraction of a composite article on whose surface a coating has been deposited. The density equation is modified to include the additional terms for the coating as follows.

$$\rho_a = v_m\cdot\rho_m + v_f\cdot\rho_f + v_p\cdot\rho_p + v_c\cdot\rho_c$$

where $v_c$ is the volume fraction of the coating, and $\rho_c$ is the mass density of the coating material.

In this case, the volume fraction of the matrix material equals 1 minus the volume fraction of the fibers minus the volume fraction of the porosity minus the volume fraction of the coating $(1-v_f-v_p-v_c)$. Applying this substitution in a similar fashion to the derivation performed for the uncoated composite article, the following equation for the volume fraction of fibers is derived.

$$v_f = [\rho_a - (1-v_p-v_c)\cdot\rho_m - v_c\cdot\rho_c]/(\rho_f-\rho_m)$$

This calculation yields the fiber volume fraction for the entire composite article, including the coating. As before, the density of the composite article and the volume fraction of the porosity are measured, and the densities of the fiber material, matrix material, and coating are obtained from reliable sources. In the present case, the volume fraction of the coating is also determined either by actual measurement or design analysis.

If the fiber volume fraction is desired for only the load-bearing composite structure beneath the coating, the previously calculated fiber volume fraction value for the entire composite article can be modified using the volume fraction of the coating as shown in the following equation.

$$v_{load\text{-}bearing\ portion} = v_f \cdot 1/(1-v_c)$$

It will be appreciated that the fiber volume fraction value for the load-bearing portion will be slightly greater than the fiber volume fraction value calculated for the entire article. The former value is usually specified in the design of composite articles.

As noted above, a preferred aspect of the invention is the measurement of the porosity within the composite article using ultrasonic waves, as will now be discussed in detail. A suitable porosity measurement system for use with this invention is based on ultrasonic immersion equipment similar to that used for inspecting metal forgings, and therefore readily available from commercial sources. However, it is believed that such systems have not been employed to inspect composite articles.

Figure 1:
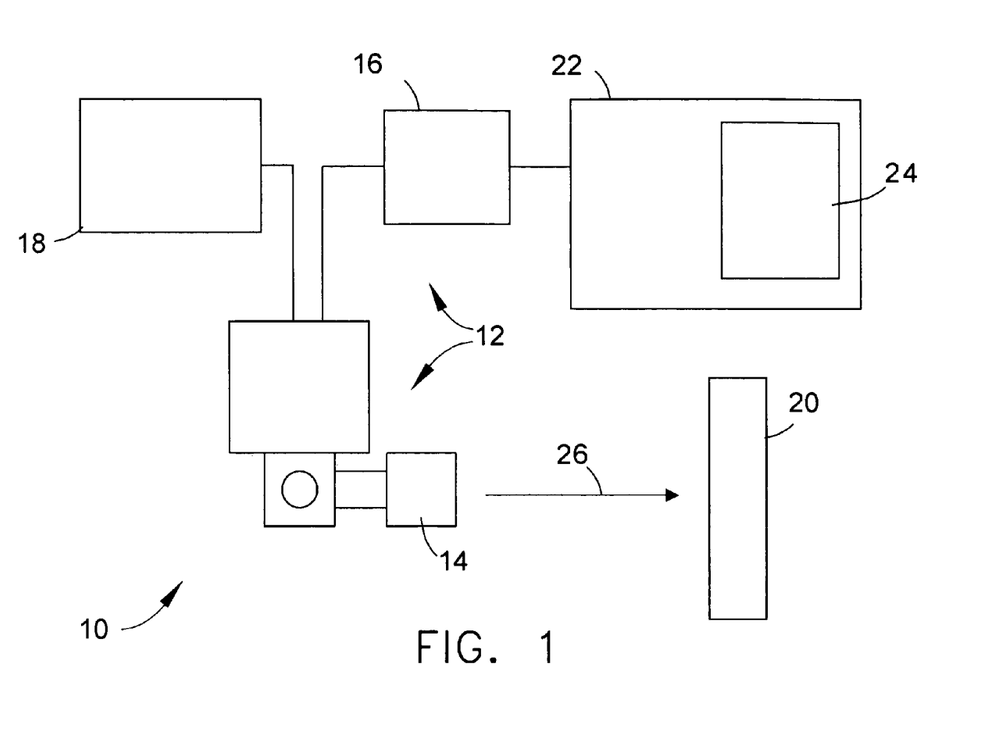
FIG. 1 schematically represents a porosity measurement system for determining the porosity in a composite structure in accordance with a preferred aspect of this invention.

FIG. 1 schematically represents a porosity measurement system 10 suitable for use in the present invention. The porosity measurement system 10 is represented as having three primary subsections: an ultrasonic system 12 comprising an ultrasonic transducer 14 for transmitting and receiving ultrasonic sound waves 26 and electronic equipment 16 for generating and amplifying signals transmitted and received by the transducer 14, a scanning system 18 for positioning the transducer 14 relative to a composite article 20 and collecting ultrasonic data therefrom, and a computer-based data collection system 22 for collecting the ultrasonic data and converting the data to digital images that can be displayed on, for example, a screen 24. Equipment of the type required by this invention is commercially available from numerous sources throughout the world, and therefore will not be described with any specificity here.

The porosity measurement system 10 of FIG. 1 uses a single ultrasonic transducer 14 for both transmitting and collecting the ultrasonic sound waves 26. It should be noted here that the use of a single transducer is common practice for ultrasonic inspection of metal bodies. During metal inspection, ultrasonic waves generated by a transducer are directly reflected by internal defects within the metal body, and the amplitude of the reflected waves are measured and characterized. For the present porosity measurement system 10, attenuation of the ultrasonic waves 26 resulting from their transmission through the composite article 20 are measured instead, necessitating different calibration and inspection procedures than those used for evaluating metal bodies.

Figure 2:
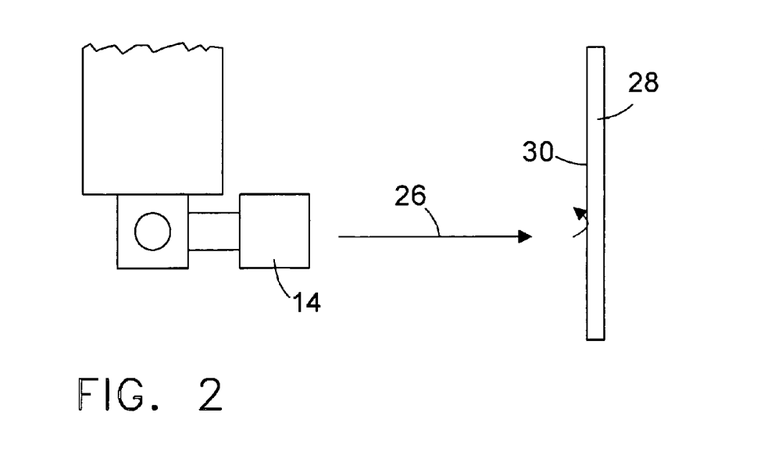
FIGS. 2 and 3 schematically depict two steps performed when determining the porosity in a composite structure in accordance with a first embodiment of this invention.
Figure 3:
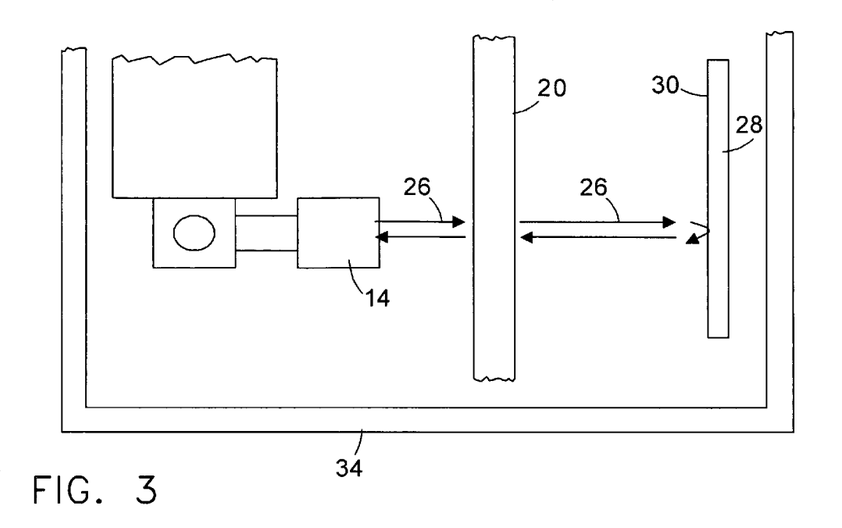

The present invention encompasses two techniques for collecting ultrasonic data and performing porosity measurements of composite articles. A first of these methods is depicted in FIGS. 2 and 3, and employs a reflector plate 28. To measure the attenuation of ultrasonic waves 26, the amplitudes of the waves 26 must be measured prior to entry into the composite article 20 and after exiting the article 20. The ratio of these amplitudes yields the attenuation of the ultrasonic waves 26 resulting from their travel through the article 20. The amplitude of the ultrasonic waves 26 as they enter the article 20 can be calculated by measuring ultrasonic waves 26 reflected from a reflector plate 28, and then correcting this value for transmission losses. FIG. 2 shows the layout of the transducer 14 and reflector plate 28 for this calibration measurement. The amplitude of the waves 26 traveling through water or another immersion fluid is determined by measuring the amplitude of the ultrasonic waves 26 reflecting off the front surface 30 of the reflector plate 28.

After these calibration data have been collected, the composite article 20 is placed in a liquid-filled immersion tank 34 for evaluation, as represented in FIG. 3. As the transducer 14 is scanned over the article 20, the amplitudes of the sound waves 26 that travel through the composite article 20, reflect off the reflector plate 28, and then travel back through the article 20 are measured and recorded. Since these waves 26 are reduced in amplitude not only by the material effects of the porosity within the article 20, but also by the sound transmission losses associated with sound traversing the two water-composite interfaces of the article 20, the amplitude of these waves 26 must be corrected to compensate for these transmission losses. For the reflector plate 28 measurement method, the correction needed is the following:

Corrected Amplitude=Measured Amplitude$\cdot[(z_1+z_2)^2/(4\cdot z_1 \cdot z_2)]^2$ Where Measured Amplitude is the signal amplitude of the ultrasonic wave 26 traveling through the composite article 20, Corrected Amplitude is the amplitude corrected for transmission losses, $z_1$ is the acoustic impedance of the immersion liquid, and $z_2$ is the acoustic impedance of the composite article 20. The derivation of this correction factor can be found in J. Krautkrämer and H. Krautkrämer; Ultrasonic Testing of Materials; Third Edition; Springer-Verlag; 1983; pages 23–26. Since the acoustic impedance of the fluid (usually water) is known and the acoustic impedance of the composite material of the article 20 is either known or measured before the inspection, this calculation becomes a simple multiplication of the collected amplitude data by a constant value.

If the composite article 20 is thick, an additional correction factor for diffraction effects may be needed. The method used for this porosity measurement system is correction by Distance Gain Size (DGS) diagram. DGS diagrams are available from most transducer manufacturers and also can be easily derived for unfocused probes using generic DGS diagrams. This correction compensates for the increase in length measured in nearfield lengths that the sound beam travels when a composite article 20 is introduced between the reflector plate 28 and the transducer 14. The travel lengths in nearfield lengths are calculated for the liquid path for the calibration measurement and for the water path and sound path through the composite article 20 for the actual porosity measurement, for which the sound path distance in near fields is the sum of the liquid path distance in nearfield lengths and the travel distance in the composite article 20 in nearfield lengths. Using a DGS diagram, the drop in amplitude due to the increased path length can be directly determined from the amplitude data for the backwall or infinite reflector line. See, for example, J. Krautkrämer and H. Krautkrämer; Ultrasonic Testing of Materials; Third Edition; Springer-Verlag; 1983; pages 90–96. The backwall gain values for both the calibration distance and the porosity measurement distance can be determined from the DGS curve. The diffraction-corrected amplitude value can be calculated as follows:

Amplitude=Corrected Amplitude$\cdot 10^{[(dBcomp-dBcal)/20]}$

Where Amplitude is the diffraction-corrected amplitude for sound wave traveling through the composite article 20, Corrected Amplitude is the previously-calculated sound amplitude corrected for transmission losses, dBcomp is the gain determined using a DGS plot for a signal at the porosity measurement path length, and dBcal is the gain determined using a DGS plot for a signal at the calibration measurement path length. For thin composite articles, this correction is small and can be neglected to simplify the measurement.

The attenuation of the ultrasonic waves 26 can now be determined using the calibration amplitude and the composite corrected amplitude or diffraction-corrected amplitude. The attenuation in decibels can be calculated as follows: $\alpha(dB)=-20\cdot\log_{10}$(Composite Amplitude/Calibration Amplitude) Where (dB) is the attenuation in decibels, Composite Amplitude is the amplitude of an ultrasonic wave 26 traveling through the composite article 20 with corrections for transmission losses and diffraction (if needed), and Calibration Amplitude is the amplitude of an ultrasonic wave 26 traveling through the immersion fluid and reflecting off the reflector plate 28.

Figure 4:
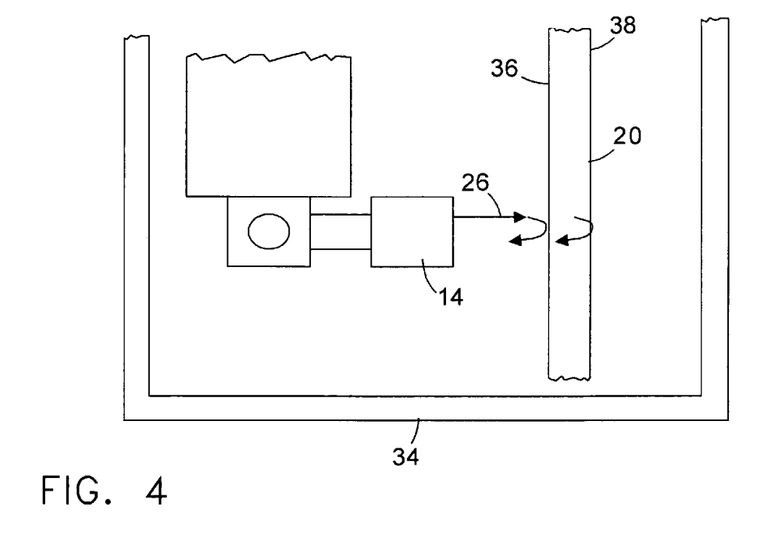
FIG. 4 schematically depicts a step performed when determining the porosity in a composite structure in accordance with a second embodiment of this invention.

The second technique for performing porosity measurements on the composite article 20 by determining the attenuation for a composite article 20 immersed in a fluid is depicted in FIG. 4. As evident from FIG. 4, this technique does not require the reflector plate 28 of the previous technique represented in FIGS. 2 and 3. The calibration amplitude of the previous technique is replaced with the reflection from the frontwall 36 of the composite article 20, and the composite measurement amplitude of the previous technique is replaced with the reflection from the backwall 38 of the article 20. The amplitude of the frontwall reflection can be used to calculate the ultrasonic wave amplitude entering the plate 28, while the backwall amplitude can be used to calculate the amplitude that is transmitted through the plate 28. In both of these cases, the amplitudes must be corrected for transmission and reflection losses.

With this method, the diffraction correction for the backwall reflection can be accomplished in a similar fashion to the correction performed with the reflector plate 28. In this case, the calibration distance is the distance in nearfield lengths between the transducer 14 and the frontwall 36 of the composite article 20. The porosity measurement distance is the calibration distance in nearfield lengths plus the thickness of the composite article 20 in nearfield lengths. The equation discussed in the previous technique can then be used to calculate the corrected backwall amplitude. Again, this correction will only be significant for thick composites and will not be necessary for thin articles.

The attenuation for the porosity measurement can be calculated directly from the frontwall reflection and either the backwall reflection or the diffraction-corrected backwall reflection. The following equation can be used to perform this measurement.

$\alpha(dB)=-20\cdot\log_{10}[($Backwall Amplitude/Frontwall Amplitude$)\cdot[(4\cdot z_1 \cdot z_2)/(z_1+z_2)^2]]$ Where (dB) is the attenuation in decibels, Backwall Amplitude is the amplitude of a reflected ultrasonic wave 26 from the backwall 38 of the composite article 20 or the diffraction-corrected value of the backwall reflection, Frontwall Amplitude is the amplitude of a ultrasonic wave 26 reflected from the frontwall 36 of the composite article 20, $z_1$ is the acoustic impedance of the immersion fluid, and $z_2$ is the acoustic impedance of the composite article 20.

Using the attenuation slope obtained from either of the ultrasonic measurement techniques described above, the porosity volume fraction ($v_p$) of the composite article 20 can be estimated using the following equation:

Porosity(%)=Coefficient$\cdot$Attenuation slope+Offset

Where Porosity is the volume percent porosity in the composite article 20 at the ultrasonic measurement location (and from which the porosity volume fraction ($v_p$) of the entire article 20 can be estimated with ultrasonic measurements taken at multiple other locations on the article 20), Coefficient is a scaling term calculated either theoretically or by experimental tests, Attenuation slope is the change in attenuation per unit thickness versus frequency, and Offset is a fitting term which is equal to the porosity value for zero attenuation slope measurements. The value of the Coefficient has been theoretically calculated and experimentally verified by others. For use on composite materials comprising graphite fibers in an epoxy matrix with unidirectional or two-dimensional lay-ups, the Coefficient value is 0.45 (percent porosity·cm·MHz/dB). Values for other composite articles have also been published and are therefore available in the literature. Likewise, the value of the Offset quantity is based on published data, and has a value of 0.4% porosity for unidirectional and two-dimensional ply graphite epoxy structures. Other values may be used to estimate porosity from the ultrasonic data. The Attenuation slope is the slope of a line fitted to the attenuation per unit thickness and the measurement frequency. For the Coefficient term used in the above equation, attenuation is given in decibels and the thickness is measured in centimeters. The frequency for the slope calculation is measured in megahertz (MHz). While previous laboratory tests on composite materials were performed by collecting attenuation data at multiple frequencies, the present invention simplifies this aspect of the nondestructive examination process to facilitate production inspections. For all theoretical calculations and most experimental tests, there exists a known attenuation versus frequency point that can be used to calculate the attenuation slope. This point is the value of attenuation at 0.0 MHz; the value of the attenuation at this point is 0.0 dB/unit length. Using this value plus one additional attenuation value measured on the composite article 20, the porosity of the article 20 can be estimated from the ultrasonic data. This simplified approach reduces the measurement time by 50% or greater when compared to previously published work.

The porosity data obtained in the above manner can be used to form a porosity image or map where the localized porosity in the article 20 can be reviewed, such as with the screen 24 represented in FIG. 1. Such a capability is not possible if a destructive technique were used to examine the contents of the article 20. The porosity image can be used to determine the quality of the article 20 and whether the article 20 is acceptable for use in critical applications.

Figure 5:
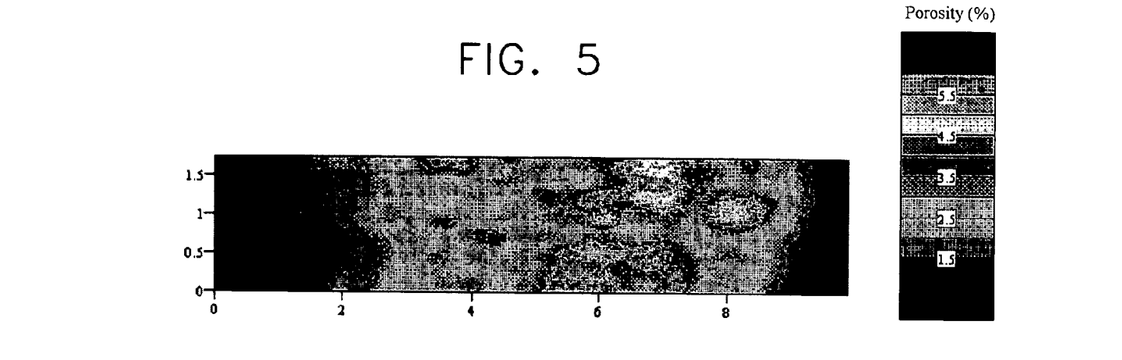
FIGS. 5, 6, and 7 are digital images generated from porosity data collecting from three specimens using methods in accordance with the present invention.

In an investigation leading to the present invention, a porosity measurement was performed using the reflector plate calibration technique with DGS diffraction correction as described above. Attenuation scans were taken of a sample graphite composite plate, and then processed to estimate the volume porosity within the plate. The plate was approximately 10.5 inches long by 2.25 inches wide by 0.273 thick (about 26.5×5.7×0.7 cm). The porosity estimate obtained by the method agreed with the results of an acid digestion examination performed on adjacent material on the plate. FIG. 5 shows a porosity image generated with the porosity data obtained from the plate. The shading represents the amount of porosity by volume. As can be seen from FIG. 5, the porosity within the plate was not uniform, with the two ends of the plate have porosity values of about 1.5% and the center of the plate having a porosity value of nearly 4%.

Figure 6:
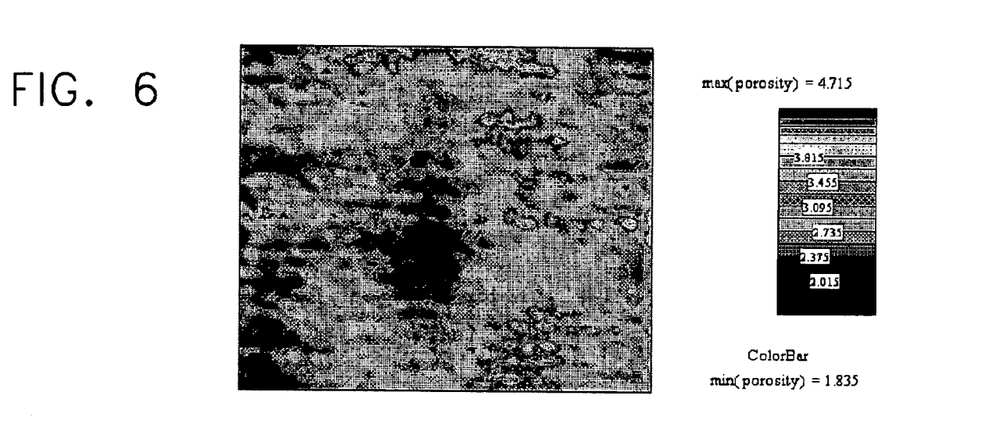

A single frequency measurement of an attenuation slope was performed with attenuation data collected from another composite plate specimen. The results of the testing showed agreement between the single frequency measurement porosity estimation and a porosity estimation obtained using multiple frequencies. FIG. 6 shows the porosity image of a flat composite test using the single frequency measurement method.

Figure 7:
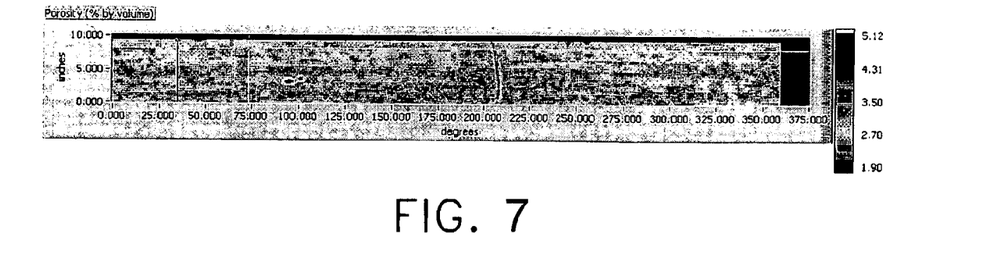

In view of the repetitive nature of the calculations performed in accordance with the porosity estimation approaches of the present invention, custom imaging and porosity calculation software was developed for use with the porosity measurement system. The software was developed to perform the calculations described above, and only required input information such as part thickness, inspection frequency, transmission losses (4.8 dB for graphite-epoxy composites), and calibration sound level. The software was used in a subsequent porosity measurement performed on composite rings. FIG. 7 shows the porosity image of one of the rings.

In combination with an ultrasonic porosity measurement technique of this invention, the fiber volume fraction of an uncoated graphite-epoxy composite panel was calculated. The density of the panel was measured to be about 1.521 g/cm$^3$. The porosity within the panel was ultrasonically measured to be about 3.3% by volume. The density of the epoxy matrix was known to be about 1.19 g/cm$^3$, and the density of the graphite fibers was known to be about 1.820 g/cm$^3$. Using the fiber volume fraction equation set forth above for examining uncoated composite articles, the fiber volume fraction was calculated to be about 58.8% as follows.

$$[\rho_a - (1-v_p)\cdot\rho_m]/(\rho_f-\rho_m) = v_f$$

$$[1.521-(1-0.033)\cdot 1.19]/(1.82-1.19) = 0.588 \text{ or } 58.8\%$$

This calculated value agreed within the measurement uncertainty to the value determined by acid digestion of adjacent material on the same panel.

The fiber volume fraction calculation technique for a coated composite was also performed. The test specimen was an experimental graphite-epoxy composite cylinder with a glass fiber coating. The density of the specimen was measured to be about 1.537 g/cm$^3$. An average porosity of about 2.52% by volume was determined using an ultrasonic porosity measurement in accordance with the present invention. The density of the resin matrix of the specimen was known to be about 1.19 g/cm$^3$, and the density of the graphite fibers was known to be about 1.82 g/cm$^3$. The density of the glass fiber coating was estimated from manufacturer's data and the design of the specimen to be about 1.63 g/cm$^3$, and the volume fraction of the coating was determined to be about 0.0483.

Using the equation for the fiber volume fraction of a load-bearing portion of a coated composite article, the fiber volume fraction was calculated to be about 59.3% as follows.

$$[\rho_a-(1-v_p-v_c)\cdot\rho_m-v_c\cdot\rho_c]/(\rho_f-\rho_m)=v_f$$

$$[1.537-(1-0.0252-0.0483)\cdot 1.19-0.0483\cdot 1.63]/(1.82-1.19)=0.564$$

$$v_f\cdot 1/(1-v_c)=v_{load\text{-}bearing\ portion}$$

$$0.564\cdot(1/1-0.0483)=0.593 \text{ or } 59.3\%$$

While the invention has been described in terms of particular embodiments, it is apparent that other forms could be adopted by one skilled in the art. Therefore, the scope of the invention is to be limited only by the following claims.

What is claimed is:

1. A method of ultrasonically inspecting an article comprising a composite material that contains porosity and a fibrous reinforcement material in a matrix material, the method comprising the steps of:

determining the mass density ($\rho_a$) of the article;

obtaining the mass density ($\rho_f$) of the fibrous reinforcement material and the mass density ($\rho_m$) of the matrix material;

ultrasonically determining the volume fraction ($v_p$) of the porosity in the article;

calculating the volume fraction ($v_f$) of the fibrous reinforcement material in the article based at least on the volume fraction ($v_p$) of the porosity in the article, the mass density ($\rho_a$) of the article, the mass density ($\rho_m$) of the matrix material, and the mass density ($\rho_f$) of the fibrous reinforcement material.

2. The method according to claim 1, wherein the article does not have a coating on a surface thereof, and the step of calculating the volume fraction ($v_f$) of the fibrous reinforcement material comprises solving the equation:

$$v_f = [(\rho_a - (1-v_p)\rho_m]/(\rho_f - \rho_m).$$

3. The method according to claim 1, wherein the article has a coating on a surface thereof, the coating has a mass density ($\rho_c$) and constitutes a volume fraction ($v_c$) of the article, and the step of calculating the volume fraction ($v_f$) of the fibrous reinforcement material comprises solving the equation:

$$v_f = [(\rho_a - (1-v_p-v_c)\rho_m - v_c\rho_c]/(\rho_f - \rho_m).$$

4. The method according to claim 1, wherein the step of ultrasonically determining the volume fraction ($v_p$) of the porosity is performed with a single ultrasonic transducer that generates and receives ultrasonic waves to determine the volume fraction ($v_p$) of the porosity.

5. The method according to claim 4, wherein the ultrasonic transducer is operated to generate a single ultrasonic frequency during the step of ultrasonically determining the volume fraction ($v_p$) of the porosity.

6. The method according to claim 1, wherein the step of ultrasonically determining the volume fraction ($v_p$) of the porosity is performed with an ultrasonic transducer that generates and receives ultrasonic waves.

7. The method according to claim 6, wherein the volume fraction ($v_p$) of the porosity is determined by measuring attenuation of the ultrasonic waves as the ultrasonic waves travel through the article.

8. The method according to claim 7, wherein attenuation of the ultrasonic waves is measured by comparing the amplitude of the ultrasonic waves prior to entering the article with the amplitude of the ultrasonic waves after exiting the article.

9. The method according to claim 8, wherein the amplitude of the ultrasonic waves prior to entering the article is measured by:

causing the ultrasonic transducer to generate ultrasonic waves toward a reflector plate; and measuring the amplitude of ultrasonic waves reflected by the reflector plate back toward the ultrasonic transducer.

10. The method according to claim 9, wherein the amplitude of the ultrasonic waves after exiting the article is measured by:

placing the article between the ultrasonic transducer and the reflector plate;

causing the ultrasonic transducer to generate ultrasonic waves through the article toward a reflector plate that reflects ultrasonic waves through the article and to the ultrasonic transducer; and measuring the amplitude of the ultrasonic waves reflected by the reflector plate through the article and to the ultrasonic transducer.

11. The method according to claim 7, wherein attenuation of the ultrasonic waves is measured by comparing the amplitude of ultrasonic waves that reflect off a first surface of the article facing the ultrasonic transducer with the amplitude of ultrasonic waves that reflect off a second surface of the article facing away from the ultrasonic transducer.

12. The method according to claim 11, wherein the amplitudes of the ultrasonic waves are measured without a separate reflector plate.

13. The method according to claim 7, wherein the attenuation measured for the ultrasonic waves is used to generate an attenuation slope and the volume fraction ($v_p$) of the porosity is calculated from the attenuation slope by solving the equation:

$$v_p = C \cdot (\text{attenuation slope}) + \text{Offset}$$

where C is a coefficient dependent on the construction of the composite material, and the offset is an empirical value.

14. The method according to claim 13, wherein the volume fraction ($v_p$) of the porosity is determined for a plurality of locations on the article to yield a plurality of porosity data, and the method further comprises the step of displaying the porosity data as a digital visual image.

15. The method according to claim 1, wherein the step of ultrasonically determining the volume fraction ($v_p$) of the porosity comprises:

immersing the article and an ultrasonic transducer in an immersion medium; and scanning the article with the ultrasonic transducer during which the ultrasonic transducer generates ultrasonic waves and receives reflected ultrasonic waves from which ultrasonic signals are collected.

16. The method according to claim 15, further comprising the step of converting the ultrasonic signals to ultrasonic data and displaying the ultrasonic data as a digital visual image.

17. A system for ultrasonically inspecting an article comprising a composite material that contains porosity and a fibrous reinforcement material in a matrix material, the article having a mass density ($\rho_a$), the fibrous reinforcement material having a mass density ($\rho_f$), and the matrix material having a mass density ($\rho_m$), the system comprising:

means for ultrasonically determining the volume fraction ($v_p$) of the porosity in the article;

means for calculating the volume fraction ($v_f$) of the fibrous reinforcement material in the article based at least on the volume fraction ($v_p$) of the porosity in the article, the mass density ($\rho_a$) of the article, the mass density ($\rho_m$) of the matrix material, and the mass density ($\rho_f$) of the fibrous reinforcement material.

18. The system according to claim 17, wherein the ultrasonically determining means comprises a single ultrasonic transducer that generates ultrasonic waves toward the article and receives ultrasonic waves reflected by the article.

19. The system according to claim 17, wherein the ultrasonically determining means further comprises means for measuring attenuation of ultrasonic waves as the ultrasonic waves travel through the article.

20. The system according to claim 17, further comprising:

an immersion medium in which the article and an ultrasonic transducer are immersed;

means for scanning the article with the ultrasonic transducer during which the ultrasonic transducer generates ultrasonic waves and receives reflected ultrasonic waves from which ultrasonic signals are collected;

means for converting the ultrasonic signals to ultrasonic data; and means for displaying the ultrasonic data as a digital visual image.

* * * * *